US008890062B2

(12) United States Patent
Campbell et al.

(10) Patent No.: US 8,890,062 B2
(45) Date of Patent: Nov. 18, 2014

(54) DIFFERENTIAL MOBILITY SPECTROMETER AND METHODS THEREOF

(71) Applicant: DH Technologies Development Pte. Ltd., Singapore (SG)

(72) Inventors: John Lawrence Campbell, Milton (CA); Yves LeBlanc, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 14/361,378

(22) PCT Filed: Nov. 21, 2012

(86) PCT No.: PCT/IB2012/002433
§ 371 (c)(1),
(2), (4) Date: May 29, 2014

(87) PCT Pub. No.: WO2013/080004
PCT Pub. Date: Jun. 6, 2013

(65) Prior Publication Data
US 2014/0264009 A1   Sep. 18, 2014

Related U.S. Application Data

(60) Provisional application No. 61/564,544, filed on Nov. 29, 2011.

(51) Int. Cl.
*H01J 49/26*   (2006.01)
*H01J 49/10*   (2006.01)
*H01J 49/06*   (2006.01)
*B01D 59/44*   (2006.01)
*G01N 27/62*   (2006.01)

(52) U.S. Cl.
CPC .................................. *G01N 27/624* (2013.01)

USPC ........................... 250/285; 250/293; 250/290

(58) Field of Classification Search
USPC .......... 250/281–283, 285, 288, 290, 292, 293
See application file for complete search history.

(56) References Cited

U.S. PATENT DOCUMENTS

| 7,598,489 B2 * | 10/2009 | Miller et al. ................ 250/292 |
| 8,158,932 B2 * | 4/2012 | Belford et al. .............. 250/287 |
| 8,692,190 B2 * | 4/2014 | Belford et al. .............. 250/287 |
| 2007/0228272 A1 | 10/2007 | Loboda |
| 2008/0116371 A1 * | 5/2008 | Wouters et al. ............. 250/288 |
| 2008/0121794 A1 * | 5/2008 | Miller et al. ................ 250/282 |
| 2008/0245963 A1 | 10/2008 | Land et al. |
| 2009/0140138 A1 | 6/2009 | Vandermey |
| 2010/0181474 A1 | 7/2010 | Wang |

FOREIGN PATENT DOCUMENTS

| JP | 2000-331641 A | 11/2000 |
| WO | 02-083276 A1 | 10/2002 |

* cited by examiner

*Primary Examiner* — Bernard E Souw

(57) ABSTRACT

An apparatus and method are provided for analyzing samples of molecules. The apparatus comprises a mass analysis system including a differential mobility spectrometer, which includes at least three filter electrodes defining two ion flow paths where the filter electrodes generate electric fields for passing through selected portions of the sample ions based on the mobility characteristics of the sample ions. The differential mobility spectrometer also includes a voltage source that provides DC and RF voltages to at least one of the filter electrodes to generate the electric field, a first and a second ion inlet that receive sample ions, and an ion outlet that outputs the selected portion of the sample ions. A mass spectrometer receives some or all of the selected portion of the sample ions.

15 Claims, 2 Drawing Sheets

DIFFERENTIAL MOBILITY SPECTROMETER AND METHODS THEREOF

RELATED APPLICATIONS

This application claims the benefit and priority of U.S. Provisional Application No. 61/564,544, filed Nov. 29, 2011, the entire teachings of which are incorporated herein by reference.

FIELD

Applicant's teachings relate to a differential mobility spectrometer and methods thereof.

INTRODUCTION

A Differential Mobility Spectrometer (DMS), also referred to as a Field Asymmetric Waveform Ion Mobility Spectrometer (FAIMS) or Field Ion Spectrometer (FIS), typically performs gas phase ion sample separation and analysis. In some circumstances, a DMS has been interfaced with a mass spectrometer (MS) to take advantage of the atmospheric pressure, gas phase, and continuous ion separation capabilities of the DMS and the detection accuracy of the MS.

By interfacing a DMS with an MS, numerous areas of sample analysis, including proteomics, peptide/protein conformation, pharmacokinetics, and metabolism analysis have been enhanced. In addition to pharmaceutical and biotech applications, DMS-based analyzers have been used for trace level explosives detection and petroleum monitoring.

A DMS, like an ion mobility spectrometer (IMS), is considered an ion mobility based analyzer because the DMS separates and analyzes ions based on the mobility characteristics of the ions. In an IMS, ions are pulsed into and pass through a drift tube while being subjected to a constant electric field. The ions interact with a drift gas in the drift tube and the interactions affect the time it takes for the sample ions to pass through the drift tube, e.g., the time-of-flight (TOF). These interactions are specific for each analyte ion of a sample, leading to an ion separation based on more than just mass/charge ratio. In contrast, in a TOF MS, there is a vacuum in the drift region of the MS and, therefore, an ion's time through the MS drift region is based on the ion's mass-to-charge ratio (m/z) in the collision-free environment of the vacuum.

A DMS is similar to an IMS in that the ions are separated in a drift gas. However, unlike an IMS, the DMS uses an asymmetric electric field waveform that is applied between two parallel electrodes through which the ions pass, typically, in a continuous manner. The electric field waveform typically has a high field duration at one polarity and then a low field duration at an opposite polarity. The duration of the high field and low field portions are applied such that the net voltage being applied to the DMS filter electrodes is zero. DMS can be used to increase the selective detection of analytes of interest in MS and MSMS analysis as it can be used to filter out unnecessary ions prior to mass analysis and only transmit analyte ions of interest. Another interesting aspect of DMS is that it can simultaneously transmit ions of opposite polarity, albeit with different optimum transmission conditions (mainly the compensation voltage used to successfully transmit ion of interest under a given set of conditions).

Another way of obtaining selective detection of information in MS and MSMS mode is to rely on ion-ion reaction performed in the vacuum of the mass spectrometer.

Ion/ion reactions, such as electron-transfer dissociation (ETD), electron capture dissociation (ECD), negative ion ETD and ECD, proton-transfer reactions (PTRs), charge-inversion reactions, and adduct formation have been employed as analytical tools for probing the structure and sequences of ionized biomolecules, such as peptides, proteins, and oligonucleotides. For example, ECD and ETD are well known to fragment ionized peptides by cleaving the peptide back-bone bonds while preserving labile post-translational modifications (PTMs) (e.g., phosphorylation, glycosylation). The most informative product ions produced in both ECD and ETD are the complementary c- and z-type fragment ions. This method differs from traditional ion fragmentation methods, such as collision-induced dissociation or infrared multi-photon dissociation, that yield b- and y-type fragment ions for ionized peptides. In addition, the latter dissociation methods often cleave the aforementioned labile PTMs from the peptide ions, thereby losing valuable information. In the field of proteomics, ETD and ECD have been used for sequencing applications in both "bottom up" (sequencing peptides from digested proteins) and "top down" (sequencing of intact proteins) scenarios.

While ion/ion reactions are renowned for their utility, there can be some drawbacks to their implementation. For example, in order to perform ion/ion reactions in a mass spectrometer, it is necessary to have ion sources of opposite polarity (one positive, the other negative) to produce the analyte ions as well as the reagent ions. This has been effectively demonstrated by using two ion sources, ESI and APCI, to provide reagent ions for both Electron-Transfer and Proton Transfer reactions. However, using two ESI sources at the same time for the generation of analyte and reagent ions has proven to be more difficult. The reasons for this impediment centre on unwanted ion-molecule reactions that occur in the source region shared by both ESI sources. For example, under commonly used analytical conditions (i.e., high liquid flow rates of >1 μL/min), large amounts of solvent vapour, including modifier and acid/base molecules, are generated from both ESI sprayers. The presence of these molecules in the source region has been shown to deplete significantly the reagent ion population and, in some cases, completely eliminate all reagent ions (e.g., dendrimer reagent ions employed in charge-inversion reactions). Hence, ion/ion reaction chemistry can be thwarted by unwanted ion-molecule reactions in the source region—before the cations and anions can even be introduced into the mass spectrometer.

SUMMARY

In various embodiments, a mass analysis system is provided having at least two ion sources for generating sample ions. In various aspects, the system comprises a differential mobility spectrometer including at least three filter electrodes defining a first ion flow path and a second ion flow path, the filter electrodes can generate electric fields for passing selected portions of the sample ions based on the mobility characteristics of the sample ions. In various embodiments, more than three filter electrodes can be provided. In various aspects the mass analysis system can include a voltage source for providing RF and DC voltages to at least one of the filter electrodes to generate the electric field. In various embodiments, a first ion inlet and a second ion inlet can be provided for receiving sample ions from at least two ion sources and an ion outlet can be provided for outputting the selected portion of the sample ions. In various aspects, the system can include a mass spectrometer for receiving some or all of the selected portion of the sample ions. In various aspects, the first inlet can receive sample ions having a first polarity and the second inlet receives sample ions having a polarity opposite to the first polarity. In various embodiments, the sample ions can have a first polarity comprising analyte ions and the sample ions can have a polarity opposite to the first polarity comprising reagent ions. In various aspects, the ions from the first and second inlets can undergo ion-ion reactions. In various embodiments, the ion-ion reactions can comprise electron transfer dissociation, negative electron transfer dissociation, proton transfer reaction, charge inversion reaction, and adduct formation. In various aspects, the ion-ion reactions can occur at the intersection of the first ion flow path and second ion flow path prior to the mass spectrometer receiving the sample ions. In various embodiments, the ion-ion reactions can occur within the mass spectrometer. In various aspects, the ions of a first and opposite polarity can be introduced into the mass spectrometer simultaneously from the first ion flow path and the second ion flow path. In various embodiments, the ions of a first and opposite polarity can be introduced into the mass spectrometer sequentially from the first ion flow path and the second ion flow path. In various aspects, the first and the second inlet can receive sample ions having the same polarity. In various embodiments, the sample ions having the same polarity can be introduced into the mass spectrometer simultaneously from the first ion flow path and the second ion flow path.

In various aspects, the sample ions having the same polarity can be introduced into the mass spectrometer sequentially from the first and the second ion flow paths.

In various embodiments, a method for mass analysis is provided. In various aspects, the method comprises providing a differential mobility spectrometer including at least three filter electrodes defining a first ion flow path and a second ion flow path, the filter electrodes can generate electric fields for passing selected portions of the sample ions based on the mobility characteristics of the sample ions. In various embodiments, more than three filter electrodes can be provided. In various aspects, the method can include providing a voltage source for providing RF and DC voltages to at least one of the filter electrodes to generate the electric field. In various embodiments, a first inlet and a second ion inlet can be provided for receiving sample ions from at least two ion sources and an ion outlet can be provided for outputting the selected portion of the sample ions. In various aspects, the method can include providing a mass spectrometer for receiving some or all of the selected portion of the sample ions. In various aspects, the first inlet can receive sample ions having a first polarity and the second inlet receives sample ions having a polarity opposite to the first polarity. In various embodiments, the sample ions can have a first polarity comprising analyte ions and the sample ions can have a polarity opposite to the first polarity comprising reagent ions. In various aspects, the ions from the first and second inlets can undergo ion-ion reactions. In various embodiments, the ion-ion reactions can comprise electron transfer dissociation, negative electron transfer dissociation, proton transfer reaction, charge inversion reaction, and adduct formation. In various aspects, the ion-ion reactions can occur at the intersection of the first and second ion flow path prior to the mass spectrometer receiving the sample ions. In various embodiments, the ion-ion reactions can occur within the mass spectrometer. In various aspects, the ions of a first and opposite polarity can be introduced into the mass spectrometer simultaneously from the first ion flow path and the second ion flow path. In various embodiments, the ions of a first and opposite polarity can be introduced into the mass spectrometer sequentially from the first ion flow path and the second ion flow path. In various aspects, the first and the second inlet can receive sample ions having the same polarity. In various embodiments, the sample ions having the same polarity can be introduced into the mass spectrometer simultaneously from the first ion flow path and the second ion flow path. In various aspects, the sample ions having the same polarity can be introduced into the mass spectrometer sequentially from the first ion flow path and the second ion flow path.

BRIEF DESCRIPTION OF THE DRAWINGS

The foregoing and other objects and advantages of the invention will be appreciated more fully from the following further description thereof, with reference to the accompanying drawings. The skilled person in the art will understand that the drawings, described below, are for illustration purposes only. The drawings are not intended to limit the scope of the applicant's teaching in any way.

DETAILED DESCRIPTION OF VARIOUS EMBODIMENTS

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

In order to address the issues described above, the applicant has realized that given the configuration of the waveforms applied to DMS electrodes, two parallel DMS devices that share a common electrode can be configured. The output of these two DMS devices can be coupled to a single mass spectrometer inlet. One result of this configuration can be the capability to introduce two or more different ion beams through each of the DMS devices simultaneously or sequentially (pulsed). In addition, these two ion beams can be of similar polarity (i.e., both beams are composed of cations) or they can be of opposite polarity (i.e., cations and anions). Precursor and reagent ions can be produced for performing ion/ion reactions. These reactions can occur at the intersection of the two DMS devices or somewhere within the mass spectrometer. The proper decoupling of the two ESI (or any other combination of two ion sources) can be accomplished with a focusing/transport device that enables control of ion introduction with some degree of selectivity prior to the mass spectrometer. This can be performed with a Differential Mobility Separation (DMS) device used in front of the mass spectrometer interface. Ideally, the DMS device would introduce ions orthogonally to the MS inlet, which would enable decoupling of the two ESI sources. A variant of this configuration could be envisaged. However, this approach would enable (1) independent control of ionization sources, (2) the prevention of any detrimental ion-molecule reactions (i.e. solvent vapor depletion of reagent ions) prior to MS introduction, and (3) focusing of ions of interest into the MS orifice. This configuration could also be used to introduce analyte and reagent ions selectively into the MS system prior to ion/ion reactions. The DMS could provide selective transfer of reagent and analyte ions to an MS system with ion/ion reactions occurring in the DMS device, which can include the intersection of the ion flow paths or within the mass spectrometer itself. Besides ion/ion reactions, this DMS device could also be employed to multiplex multiple ion sources or to allow the simultaneous or sequential introduction of calibrant ions into the mass spectrometer.

Figure 1:
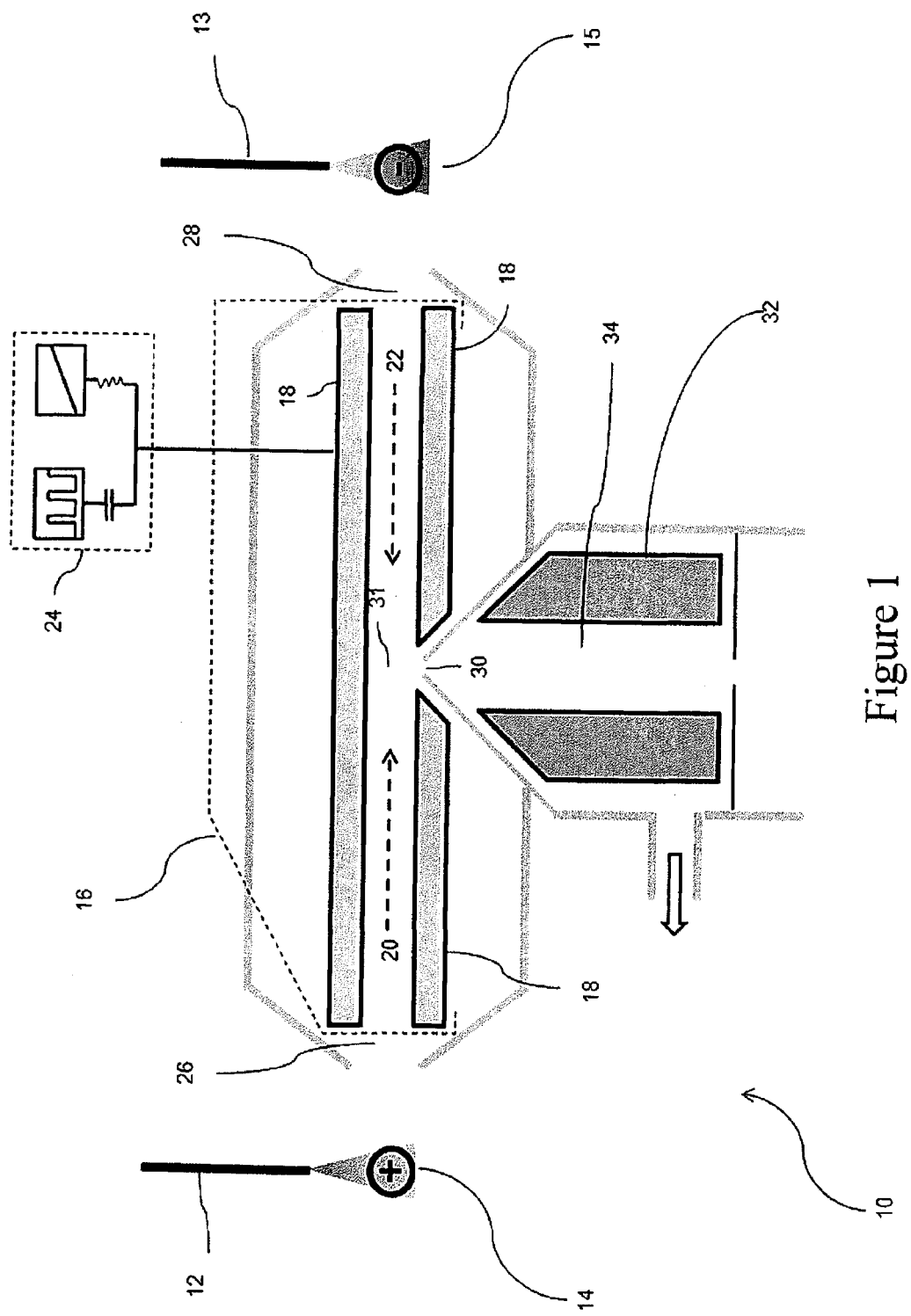
FIG. 1 schematically illustrates a mass analysis system in accordance with various embodiments of the applicant's teachings.
Figure 2:
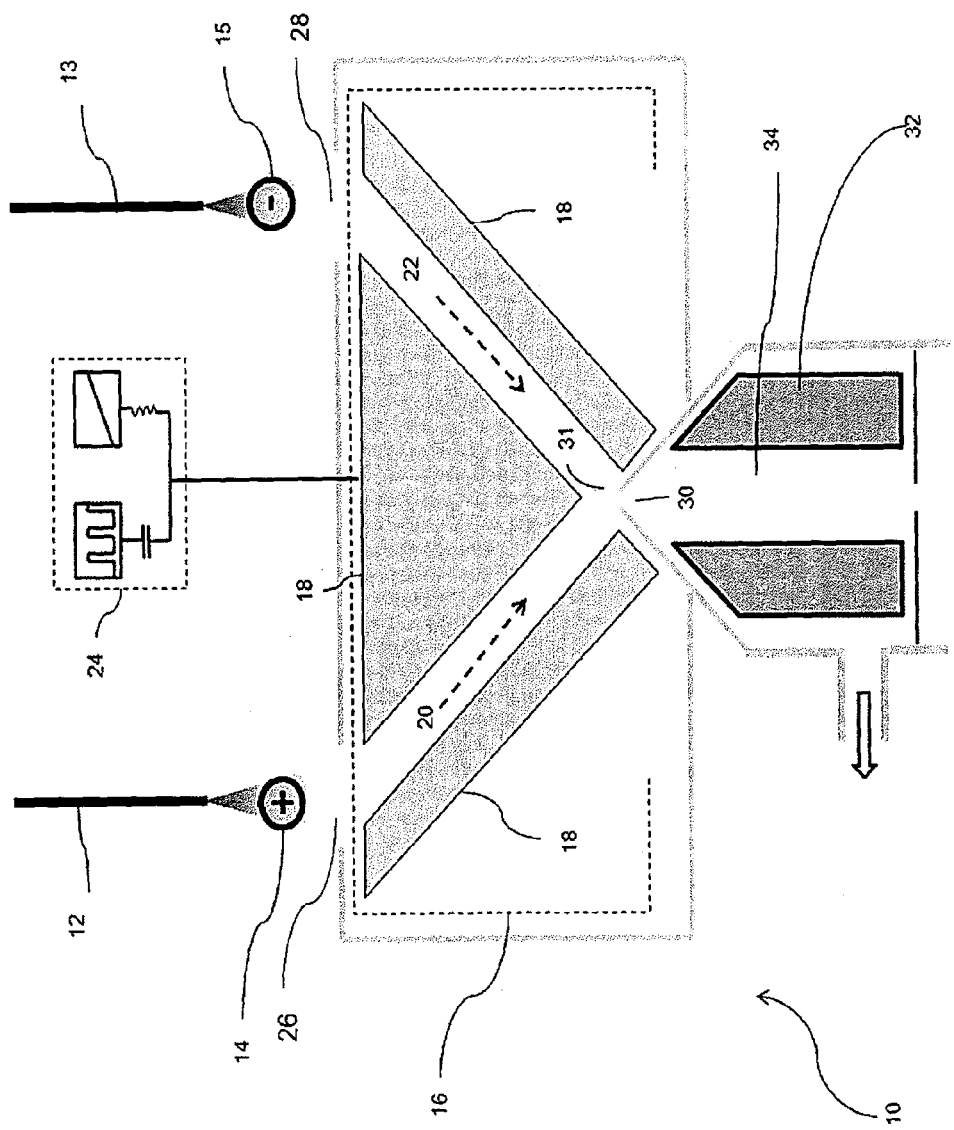
FIG. 2 schematically illustrates a mass analysis system in accordance with various embodiments of the applicant's teachings.

According to various embodiments to the applicant's teachings, a system and method are provided for mass analysis. Reference is made to FIGS. 1 and 2 exemplifying various configurations of a mass analysis system 10 having at least two ion sources 12 and 13 for generating sample ions 14 and 15. In various aspects, any suitable ion source can be used, including, but not limited to, an electrospray ionization (ESI), matrix-assisted laser-desorption ionization (MALDI), laser desorption-ionization, electron ionization, atmospheric pressure chemical ionization (APCI), photospray, chemical ionization (CI), secondary ion mass spectrometry (SIMS), fast atom bombardment (FAB), laserspray, and inlet ionization. In various aspects, the system comprises a differential mobility spectrometer 16 including at least three filter electrodes 18 defining a first ion flow path 20 and a second ion flow path 22. In various embodiments, more than three filter electrodes can be provided. In various embodiments, the filter electrodes 18 can generate electric fields for passing selected portions of the sample ions 14 and 15 based on the mobility characteristics of the sample ions 14 and 15. In various aspects, the mass analysis system 16 can include a voltage source 24 for providing RF and DC voltages to at least one of the filter electrodes 18 to generate the electric field. In various embodiments, a first ion inlet 26 and a second ion inlet 28 can be provided for receiving sample ions 14 and 15 from at least two ion sources 12 and 13 and an ion outlet 30 can be provided for outputting the selected portion of the sample ions 14 and 15. In various aspects, a mass spectrometer 32 can receive some or all of the selected portion of the sample ions 14 and 15. In various aspects, the mass spectrometer can include, but is not limited to, a quadrupole, hexapole, octapole, or other multipole, a 3D quadrupole ion trap, a 2D linear ion trap, an ion cyclotron trap, a C-trap, an Orbitrap, an electrostatic ion trap, or a time-of-flight (ToF) MS. In various aspects, the first inlet 26 can receive sample ions 14 having a first polarity and the second inlet 28 receives sample ions 15 having a polarity opposite to the first polarity. In various embodiments, the sample ions can have a first polarity comprising analyte ions and the sample ions can have a polarity opposite to the first polarity comprising reagent ions. In various aspects, the ions from the first 26 and second 28 inlets can undergo ion-ion reactions. In various aspects, any suitable ion/ion reaction can be performed, including, but not limited to, electron transfer dissociation, negative ion electron transfer dissociation, proton transfer reaction, charge inversion reaction, and adduct formation. In various embodiments, the ion-ion reactions can comprise electron transfer dissociation, negative electron transfer dissociation, proton transfer reaction, charge inversion reaction, and adduct formation. In various aspects, the ion-ion reactions can occur in the DMS device 16. In various embodiments, the ion-ion reactions can occur at the intersection 31 of the first 20 and second 22 ion flow paths prior to the mass spectrometer 32 receiving the sample ions. In various embodiments, the ion-ion reactions can occur at the ion outlet 30 or within the mass spectrometer 32 including, but not limited to Q0, Q1, Q2, Q3, an interquad lens or any combinations thereof. In various aspects, an ion/ion reaction can be performed in a given mode, including, but not limited to, mutual storage mode or transmission mode as known in the art and described in Analytical Chemistry, 2007, 79, pgs. 3363-3370, hereinafter incorporated by reference. In various aspects, the ions of a first and opposite polarity can be introduced into the mass spectrometer 32 simultaneously from the first 20 and the second 22 ion flow paths. In various embodiments, the ions 14 and 15 of a first and opposite polarity can be introduced into the mass spectrometer 32 sequentially from the first 20 and the second 22 ion flow paths. In various embodiments, the sample ions 14 and 15 having the same polarity can be introduced into the mass spectrometer 32 simultaneously from the first 20 and the second 22 ion flow paths. In various aspects, the sample ions 14 and 15 having the same polarity can be introduced into the mass spectrometer 32 sequentially from the first 20 and the second 22 ion flow paths.

In use, sample ions 14 and 15 can be generated by at least two ion sources 12 and 13. In various aspects, any suitable ion source can be used, including, but not limited to, an electrospray ionization (ESI), matrix-assisted laser-desorption ionization (MALDI), laser desorption-ionization, electron ionization, atmospheric pressure chemical ionization (APCI), photospray, chemical ionization (CI), secondary ion mass spectrometry (SIMS), fast atom bombardment (FAB), laserspray, and inlet ionization.

The sample ions pass through a first ion inlet 26 and a second ion inlet 28. In various embodiments, the sample ions 14 that pass through the first ion inlet 26 can be of a first polarity and the sample ions 15 that pass through the second ion inlet 28 can be of an opposite polarity to the ions 14 of a first polarity. In various embodiments, the sample ions 14 and 15 can be of the same polarity. In various aspects, a differential mobility spectrometer 16 can be provided comprising at least three filter electrodes 18. In various embodiments, more than three filter electrodes can be provided. The filter electrodes 18 define a first ion flow path 20 and a second ion flow path 22. In various embodiments a voltage source 24 can provide RF and DC voltages to at least one of the filter electrodes to generate the electric field. The sample ions 14 and 15 can pass through the first 20 and second 22 ion flow paths, and ion-ion reactions can occur within the DMS 16 or, in various aspects, at intersection 31 of the first 20 and second 22 ion flow paths. In various aspects, any suitable ion/ion reaction can be performed, including, but not limited to, electron transfer dissociation, negative ion electron transfer dissociation, proton transfer reaction, charge inversion reaction, and adduct formation. The ions then pass through ion outlet 30 and can enter the mass spectrometer 32. In various aspects, the mass spectrometer can include, but is not limited to, a quadrupole, hexapole, octapole, or other multipole, a 3D quadrupole ion trap, a 2D linear ion trap, an ion cyclotron trap, a C-trap, an Orbitrap, an electrostatic ion trap, or a time-of-flight (ToF) MS. In various embodiments, the ions can further react within the mass spectrometer, as exemplified by reference numeral 34 in FIGS. 1 and 2. In various embodiments, the sample ions 14 and 15 generated by the at least two ion sources 12 and 13 and which can be of either the opposite or the same polarities can pass through the first 26 and the second 28 ion inlets. In various aspects, the sample ions 14 and 15 can pass through ion outlet 30 and enter the mass spectrometer 32. In various embodiments, the sample ions 14 and 15 can undergo ion-ion reactions within the system, including, but not limited to, anywhere along the first 20 and second 22 ion flow paths, at the ion outlet 30, and within the mass spectrometer 32 including, but not limited to Q0, Q1, Q2, Q3, an interquad lens or any combinations thereof. In various aspects, any suitable ion/ion reaction can be performed, including, but not limited to, electron transfer dissociation, negative ion electron transfer dissociation, proton transfer reaction, charge inversion reaction, and adduct formation. In various aspects, an ion/ion reaction can be performed in a given mode, including, but not limited to, mutual storage mode or transmission mode.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

The invention claimed is:

1. A mass analysis system comprising:
    at least two ion sources for generating sample ions;
        a differential mobility spectrometer including:
    at least three filter electrodes defining a first ion flow path and a second ion flow path, the filter electrodes generating electric fields for passing selected portions of the sample ions based on the mobility characteristics of the sample ions;
        a voltage source for providing RF and DC voltages to at least one of the filter electrodes to generate the electric field;
        a first and a second ion inlet for receiving sample ions from the at least two ion sources; and
        an ion outlet for outputting the selected portion of the sample ions, and
        a mass spectrometer for receiving some or all of the selected portion of the sample ions.

2. The system of claim 1, wherein the first inlet receives sample ions having a first polarity and the second inlet receives sample ions having a polarity opposite to the first polarity.

3. The system of claim 2, wherein the sample ions having a first polarity comprise analyte ions and the sample ions having a polarity opposite to the first polarity comprise reagent ions.

4. The system of claim 3, wherein the ions from the first and second inlets undergo ion-ion reactions.

5. The system of claim 4 wherein the ion-ion reactions comprise one or more of electron transfer dissociation, negative electron transfer dissociation, proton transfer reaction, charge inversion reaction, and adduct formation.

6. The system of claim 4, wherein the ion-ion reactions occur at the intersection of the first and the second ion flow paths prior to the mass spectrometer receiving the sample ions.

7. The system of claim 4, wherein the ion-ion reactions occur within the mass spectrometer.

8. The system of claim 7, wherein the ions of a first and opposite polarity are introduced into the mass spectrometer simultaneously from the first and the second ion flow paths.

9. The system of claim 7, wherein the ions of a first and opposite polarity are introduced into the mass spectrometer sequentially from the first and the second ion flow paths.

10. The system of claim 1, wherein the first and the second inlet receive sample ions having the same polarity.

11. The system of claim 10, wherein the sample ions having the same polarity are introduced into the mass spectrometer simultaneously from the first and the second ion flow paths.

12. The system of claim 10, wherein the sample ions having the same polarity are introduced into the mass spectrometer sequentially from the first and the second ion flow paths.

13. A method of mass analysis comprising providing a mass analysis system of any of claims 1 to 12.

14. A method of mass analysis comprising:
    generating first and second sample ions from at least two ion sources;
    sending first and second sample ions from the first and second ion sources through first and second ion inlets, respectively, of a differential mobility spectrometer:
the differential mobility spectrometer including at least three filter electrodes defining a first ion flow path for the first sample ions and a second ion flow path for the second sample ions, the filter electrodes generating electric fields for passing selected portions of the sample ions based on the mobility characteristics of the sample ions;
    providing a voltage source for providing RF and DC voltages to at least one of the filter electrodes to generate the electric field;
    providing an ion outlet for outputting the selected portion of the sample ions, and
    providing a mass spectrometer for receiving some or all of the selected portion of the sample ions.

15. The method of claim 14, wherein the first inlet receives sample ions having a first polarity and the second inlet receives sample ions having a polarity opposite to the first polarity and said first and second ions undergoing ion-ion reactions.

* * * * *